United States Patent
Brunner et al.

(10) Patent No.: US 9,669,079 B2
(45) Date of Patent: *Jun. 6, 2017

(54) PCSK9 PEPTIDE COMBINATION VACCINE AND METHOD OF USE

(71) Applicant: AFFIRIS AG, Vienna (AT)

(72) Inventors: Sylvia Brunner, Vienna (AT); Gergana Galabova, Vienna (AT); Bettina Wanko, Vienna (AT); Markus Windwarder, Vienna (AT); Gabriele Winsauer, Vienna (AT); Guenther Staffler, Vienna (AT); Claudia Juno, Vienna (AT)

(73) Assignee: AFFIRIS AG, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/921,485

(22) Filed: Oct. 23, 2015

(65) Prior Publication Data

US 2016/0106822 A1    Apr. 21, 2016

Related U.S. Application Data

(62) Division of application No. 14/344,879, filed as application No. PCT/EP2012/067950 on Sep. 13, 2012, now Pat. No. 9,220,762.

(30) Foreign Application Priority Data

Sep. 13, 2011    (EP) ..................... 11181090

(51) Int. Cl.
| | | |
|---|---|---|
| *A61K 39/00* | (2006.01) | |
| *A61K 39/39* | (2006.01) | |
| *C12N 9/64* | (2006.01) | |
| *C07K 16/40* | (2006.01) | |
| *A61K 39/385* | (2006.01) | |

(52) U.S. Cl.
CPC ...... *A61K 39/0005* (2013.01); *A61K 39/0012* (2013.01); *A61K 39/385* (2013.01); *A61K 39/39* (2013.01); *C07K 16/40* (2013.01); *C12N 9/6454* (2013.01); *A61K 2039/54* (2013.01); *A61K 2039/545* (2013.01); *A61K 2039/55505* (2013.01); *A61K 2039/6081* (2013.01); *C07K 2317/34* (2013.01); *C07K 2319/00* (2013.01); *C07K 2319/21* (2013.01); *C07K 2319/23* (2013.01); *C07K 2319/40* (2013.01); *C07K 2319/50* (2013.01); *C12Y 304/21061* (2013.01)

(58) Field of Classification Search
None
See application file for complete search history.

(56) References Cited

U.S. PATENT DOCUMENTS

| | | |
|---|---|---|
| 2009/0246192 A1 | 10/2009 | Condra et al. |
| 2011/0052621 A1 | 3/2011 | Champion et al. |
| 2012/0301461 A1 | 11/2012 | Condra et al. |

FOREIGN PATENT DOCUMENTS

| | | |
|---|---|---|
| WO | 2009 100297 | 8/2009 |
| WO | 2010 057242 | 5/2010 |
| WO | 2011 027257 | 3/2011 |

OTHER PUBLICATIONS

Galabova et al.—"Peptide-Based Anti-PCSK9 Vaccines—An Approach for Long-Term LDLc Management", Dec. 4, 2014, PLOS One 9(12): 1-18,e114469, DOI:10.1371/journal.pone.0114469, 18 pages.
Chan et al.—"A Proprotein convertase subtilisin/kexin type 9 neutralizing antibody reduces serum cholesterol in mice and nonhuman primates", Jun. 16, 2009, PNAS 106(24):9820-9825.
Urnan et al.—"Targeting the Proprotein Convertase Subtilisin/Kexin Type 9 for the Treatment of Dyslipidemia and Atherosclerosis", Oct. 15, 2013, Journal of the American College of Cardiology 62(16): 1401-1408.
Singh, M. et al., "Advances in vaccine adjuvants" Nat. Biotech. vol. 17, pp. 1075-1081, Nov. 1999.
O'Hagan, D. T. et al., "Recent Advances in the Discovery and Delivery of Vaccine Adjuvants" Nature Reviews, Drug Discovery, vol. 2, pp. 727-735, Sep. 2003.
Hermanson, G. T., "Bioconjugate Techniques" Second Edition, Elsevier, 1233 p. 2008.
Niazi, S. K., "Handbook of Pharmaceutical Manufacturing Formulations" CRC Press Inc., vol. 4, 277 p. 2004.
Steinberg, D. , "An interpretive history of the cholesterol controversy: part II: the early evidence linking hypercholesterolemia to coronary disease in humans[1]" Journal of Lipid Research, vol. 46, pp. 179-190, 2005.
Steinberg, D. , "An interpretive history of the cholesterol controversy, part V: The discovery of the statins and the end of the controversy" Journal of Lipid Research, vol. 47, pp. 1339-1351, 2006.
International Search Report Issued Mar. 15, 2013 in PCT/EP12/067950 filed Sep. 13, 2012.
European Search Report Issued Jun. 15,2012 in European Patent Application No. 11181090.9 filed Sep. 13, 2011.
Written Opinion of the International Searching Authority Issued Mar. 15, 2013 in PCT/EP12/067950 filed Sep. 13, 2012.

*Primary Examiner* — John Ulm
(74) *Attorney, Agent, or Firm* — Oblon, McClelland, Maier & Neustadt, L.L.P.

(57) ABSTRACT

The present invention relates to a immunogen comprising at least two fragments of Proprotein convertase subtilisin/kexin type 9 (PCSK9), wherein at least two fragments comprise at least 8 consecutive amino acid residues of amino acid residues 150 to 170 and/or 205 to 225 of PCSK9 (SEQ ID NO:9).

20 Claims, 2 Drawing Sheets

SEQUENCE LISTING

<160> NUMBER OF SEQ ID NOS: 45

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide PCSK9 fragment

<400> SEQUENCE: 1

Arg Pro Glu Thr Trp Ile Pro Asn Arg Ser Pro Ile Leu
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide PCSK9 fragment

<400> SEQUENCE: 2

Ser Ile Pro Trp Asn Leu Glu Arg Ile Thr Pro Pro Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide PCSK9 fragment

<400> SEQUENCE: 3

Pro Glu Glu Asp Gly Thr Arg Phe His Arg Gln Ala Ser Lys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide PCSK9 fragment

<400> SEQUENCE: 4

Pro Glu Glu Asp Gly Thr Arg Phe His Arg Gln Ala
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic peptide PCSK9 fragment

<400> SEQUENCE: 5

Glu Glu Asp Gly Thr Arg Phe His Arg Gln Ala Ser Lys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide PCSK9 fragment

<400> SEQUENCE: 6

Glu Glu Asp Gly Thr Arg Phe His Arg Gln Ala Ser
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide PCSK9 fragment

<400> SEQUENCE: 7

Ser Ile Pro Trp Asn Leu Glu Arg Ile Thr Pro
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide PCSK9 fragment

<400> SEQUENCE: 8

```
Ser Ile Pro Trp Asn Leu Glu Arg Ile Thr
1               5                   10
```

<210> SEQ ID NO 9
<211> LENGTH: 692
<212> TYPE: PRT
<213> ORGANISM: Homo sapiens

<400> SEQUENCE: 9

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320
```

-continued

```
Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 10
<211> LENGTH: 20
<212> TYPE: PRT
<213> ORGANISM: Artificial Sequence
<220> FEATURE:
```

<223> OTHER INFORMATION: Synthetic peptide PCSK9 fragment

<400> SEQUENCE: 10

Phe Ala Gln Ser Ile Pro Trp Asn Leu Glu Arg Ile Thr Pro Pro Arg
1               5                   10                  15

Tyr Arg Ala Asp
            20

<210> SEQ ID NO 11
<211> LENGTH: 19
<212> TYPE: PRT
<213> ORGANISM: Artificial Sequence
<220> FEATURE:
<223> OTHER INFORMATION: Synthetic peptide PCSK9 fragment

<400> SEQUENCE: 11

Phe Ala Gln Ser Ile Pro Trp Asn Leu Glu Arg Ile Thr Pro Pro Arg
1               5                   10                  15

Tyr Arg Ala

<210> SEQ ID NO 12
<211> LENGTH: 18
<212> TYPE: PRT
<213> ORGANISM: Artificial Sequence
<220> FEATURE:
<223> OTHER INFORMATION: Synthetic peptide PCSK9 fragment

<400> SEQUENCE: 12

Phe Ala Gln Ser Ile Pro Trp Asn Leu Glu Arg Ile Thr Pro Pro Arg
1               5                   10                  15

Tyr Arg

<210> SEQ ID NO 13
<211> LENGTH: 17
<212> TYPE: PRT
<213> ORGANISM: Artificial Sequence
<220> FEATURE:
<223> OTHER INFORMATION: Synthetic peptide PCSK9 fragment

<400> SEQUENCE: 13

Phe Ala Gln Ser Ile Pro Trp Asn Leu Glu Arg Ile Thr Pro Pro Arg
1               5                   10                  15

Tyr

<210> SEQ ID NO 14
<211> LENGTH: 16
<212> TYPE: PRT
<213> ORGANISM: Artificial Sequence
<220> FEATURE:
<223> OTHER INFORMATION: Synthetic peptide PCSK9 fragment

<400> SEQUENCE: 14

Phe Ala Gln Ser Ile Pro Trp Asn Leu Glu Arg Ile Thr Pro Pro Arg
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide PCSK9 fragment

<400> SEQUENCE: 15

Phe Ala Gln Ser Ile Pro Trp Asn Leu Glu Arg Ile Thr Pro Pro

```
                        1               5                   10                  15

<210> SEQ ID NO 16
<211> LENGTH: 19
<212> TYPE: PRT
<213> ORGANISM: Artificial Sequence
<220> FEATURE:
<223> OTHER INFORMATION: Synthetic peptide PCSK9 fragment

<400> SEQUENCE: 16

Ala Gln Ser Ile Pro Trp Asn Leu Glu Arg Ile Thr Pro Pro Arg Tyr
1               5                   10                  15

Arg Ala Asp

<210> SEQ ID NO 17
<211> LENGTH: 18
<212> TYPE: PRT
<213> ORGANISM: Artificial Sequence
<220> FEATURE:
<223> OTHER INFORMATION: Synthetic peptide PCSK9 fragment

<400> SEQUENCE: 17

Gln Ser Ile Pro Trp Asn Leu Glu Arg Ile Thr Pro Pro Arg Tyr Arg
1               5                   10                  15

Ala Asp

<210> SEQ ID NO 18
<211> LENGTH: 17
<212> TYPE: PRT
<213> ORGANISM: Artificial Sequence
<220> FEATURE:
<223> OTHER INFORMATION: Synthetic peptide PCSK9 fragment

<400> SEQUENCE: 18

Ser Ile Pro Trp Asn Leu Glu Arg Ile Thr Pro Pro Arg Tyr Arg Ala
1               5                   10                  15

Asp

<210> SEQ ID NO 19
<211> LENGTH: 18
<212> TYPE: PRT
<213> ORGANISM: Artificial Sequence
<220> FEATURE:
<223> OTHER INFORMATION: Synthetic peptide PCSK9 fragment

<400> SEQUENCE: 19

Ala Gln Ser Ile Pro Trp Asn Leu Glu Arg Ile Thr Pro Pro Arg Tyr
1               5                   10                  15

Arg Ala

<210> SEQ ID NO 20
<211> LENGTH: 17
<212> TYPE: PRT
<213> ORGANISM: Artificial Sequence
<220> FEATURE:
<223> OTHER INFORMATION: Synthetic peptide PCSK9 fragment

<400> SEQUENCE: 20

Gln Ser Ile Pro Trp Asn Leu Glu Arg Ile Thr Pro Pro Arg Tyr Arg
1               5                   10                  15

Ala

<210> SEQ ID NO 21
```

-continued

```
<211> LENGTH: 16
<212> TYPE: PRT
<213> ORGANISM: Artificial Sequence
<220> FEATURE:
<223> OTHER INFORMATION: Synthetic peptide PCSK9 fragment

<400> SEQUENCE: 21

Ser Ile Pro Trp Asn Leu Glu Arg Ile Thr Pro Pro Arg Tyr Arg Ala
1               5                   10                  15

<210> SEQ ID NO 22
<211> LENGTH: 17
<212> TYPE: PRT
<213> ORGANISM: Artificial Sequence
<220> FEATURE:
<223> OTHER INFORMATION: Synthetic peptide PCSK9 fragment

<400> SEQUENCE: 22

Ala Gln Ser Ile Pro Trp Asn Leu Glu Arg Ile Thr Pro Pro Arg Tyr
1               5                   10                  15

Arg

<210> SEQ ID NO 23
<211> LENGTH: 16
<212> TYPE: PRT
<213> ORGANISM: Artificial Sequence
<220> FEATURE:
<223> OTHER INFORMATION: Synthetic peptide PCSK9 fragment

<400> SEQUENCE: 23

Gln Ser Ile Pro Trp Asn Leu Glu Arg Ile Thr Pro Pro Arg Tyr Arg
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide PCSK9 fragment

<400> SEQUENCE: 24

Ser Ile Pro Trp Asn Leu Glu Arg Ile Thr Pro Pro Arg Tyr Arg
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide PCSK9 fragment

<400> SEQUENCE: 25

Gln Ser Ile Pro Trp Asn Leu Glu Arg Ile Thr Pro Pro Arg Tyr
1               5                   10                  15

<210> SEQ ID NO 26
<211> LENGTH: 14
<212> TYPE: PRT
<213> ORGANISM: Artificial Sequence
<220> FEATURE:
<223> OTHER INFORMATION: Synthetic peptide PCSK9 fragment

<400> SEQUENCE: 26

Ser Ile Pro Trp Asn Leu Glu Arg Ile Thr Pro Pro Arg Tyr
1               5                   10
```

```
<210> SEQ ID NO 27
<211> LENGTH: 15
<212> TYPE: PRT
<213> ORGANISM: Artificial Sequence
<220> FEATURE:
<223> OTHER INFORMATION: Synthetic peptide PCSK9 fragment

<400> SEQUENCE: 27

Ala Gln Ser Ile Pro Trp Asn Leu Glu Arg Ile Thr Pro Pro Arg
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: Synthetic peptide PCSK9 fragment

<400> SEQUENCE: 28

Gln Ser Ile Pro Trp Asn Leu Glu Arg Ile Thr Pro Pro Arg
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic peptide PCSK9 fragment

<400> SEQUENCE: 29

Ser Ile Pro Trp Asn Leu Glu Arg Ile Thr Pro Pro
1               5                   10

<210> SEQ ID NO 30
<211> LENGTH: 20
<212> TYPE: PRT
<213> ORGANISM: Artificial Sequence
<220> FEATURE:
<223> OTHER INFORMATION: Synthetic peptide PCSK9 fragment

<400> SEQUENCE: 30

Glu Asn Val Pro Glu Glu Asp Gly Thr Arg Phe His Arg Gln Ala Ser
1               5                   10                  15

Lys Cys Asp Ser
            20

<210> SEQ ID NO 31
<211> LENGTH: 19
<212> TYPE: PRT
<213> ORGANISM: Artificial Sequence
<220> FEATURE:
<223> OTHER INFORMATION: Synthetic peptide PCSK9 fragment

<400> SEQUENCE: 31

Glu Asn Val Pro Glu Glu Asp Gly Thr Arg Phe His Arg Gln Ala Ser
1               5                   10                  15

Lys Cys Asp

<210> SEQ ID NO 32
<211> LENGTH: 18
<212> TYPE: PRT
<213> ORGANISM: Artificial Sequence
<220> FEATURE:
<223> OTHER INFORMATION: Synthetic peptide PCSK9 fragment

<400> SEQUENCE: 32
```

Glu Asn Val Pro Glu Glu Asp Gly Thr Arg Phe His Arg Gln Ala Ser
1               5                   10                  15

Lys Cys

<210> SEQ ID NO 33
<211> LENGTH: 17
<212> TYPE: PRT
<213> ORGANISM: Artificial Sequence
<220> FEATURE:
<223> OTHER INFORMATION: Synthetic peptide PCSK9 fragment

<400> SEQUENCE: 33

Glu Asn Val Pro Glu Glu Asp Gly Thr Arg Phe His Arg Gln Ala Ser
1               5                   10                  15

Lys

<210> SEQ ID NO 34
<211> LENGTH: 19
<212> TYPE: PRT
<213> ORGANISM: Artificial Sequence
<220> FEATURE:
<223> OTHER INFORMATION: Synthetic peptide PCSK9 fragment

<400> SEQUENCE: 34

Asn Val Pro Glu Glu Asp Gly Thr Arg Phe His Arg Gln Ala Ser Lys
1               5                   10                  15

Cys Asp Ser

<210> SEQ ID NO 35
<211> LENGTH: 18
<212> TYPE: PRT
<213> ORGANISM: Artificial Sequence
<220> FEATURE:
<223> OTHER INFORMATION: Synthetic peptide PCSK9 fragment

<400> SEQUENCE: 35

Val Pro Glu Glu Asp Gly Thr Arg Phe His Arg Gln Ala Ser Lys Cys
1               5                   10                  15

Asp Ser

<210> SEQ ID NO 36
<211> LENGTH: 17
<212> TYPE: PRT
<213> ORGANISM: Artificial Sequence
<220> FEATURE:
<223> OTHER INFORMATION: Synthetic peptide PCSK9 fragment

<400> SEQUENCE: 36

Pro Glu Glu Asp Gly Thr Arg Phe His Arg Gln Ala Ser Lys Cys Asp
1               5                   10                  15

Ser

<210> SEQ ID NO 37
<211> LENGTH: 18
<212> TYPE: PRT
<213> ORGANISM: Artificial Sequence
<220> FEATURE:
<223> OTHER INFORMATION: Synthetic peptide PCSK9 fragment

<400> SEQUENCE: 37

Asn Val Pro Glu Glu Asp Gly Thr Arg Phe His Arg Gln Ala Ser Lys
1               5                   10                  15

Cys Asp

<210> SEQ ID NO 38
<211> LENGTH: 17
<212> TYPE: PRT
<213> ORGANISM: Artificial Sequence
<220> FEATURE:
<223> OTHER INFORMATION: Synthetic peptide PCSK9 fragment

<400> SEQUENCE: 38

Val Pro Glu Glu Asp Gly Thr Arg Phe His Arg Gln Ala Ser Lys Cys
1               5                   10                  15

Asp

<210> SEQ ID NO 39
<211> LENGTH: 16
<212> TYPE: PRT
<213> ORGANISM: Artificial Sequence
<220> FEATURE:
<223> OTHER INFORMATION: Synthetic peptide PCSK9 fragment

<400> SEQUENCE: 39

Pro Glu Glu Asp Gly Thr Arg Phe His Arg Gln Ala Ser Lys Cys Asp
1               5                   10                  15

<210> SEQ ID NO 40
<211> LENGTH: 17
<212> TYPE: PRT
<213> ORGANISM: Artificial Sequence
<220> FEATURE:
<223> OTHER INFORMATION: Synthetic peptide PCSK9 fragment

<400> SEQUENCE: 40

Asn Val Pro Glu Glu Asp Gly Thr Arg Phe His Arg Gln Ala Ser Lys
1               5                   10                  15

Cys

<210> SEQ ID NO 41
<211> LENGTH: 16
<212> TYPE: PRT
<213> ORGANISM: Artificial Sequence
<220> FEATURE:
<223> OTHER INFORMATION: Synthetic peptide PCSK9 fragment

<400> SEQUENCE: 41

Val Pro Glu Glu Asp Gly Thr Arg Phe His Arg Gln Ala Ser Lys Cys
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic peptide PCSK9 fragment

<400> SEQUENCE: 42

Pro Glu Glu Asp Gly Thr Arg Phe His Arg Gln Ala Ser Lys Cys
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic peptide PCSK9 fragment

<400> SEQUENCE: 43

```
Asn Val Pro Glu Glu Asp Gly Thr Arg Phe His Arg Gln Ala Ser Lys
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic peptide PCSK9 fragment

<400> SEQUENCE: 44

Val Pro Glu Glu Asp Gly Thr Arg Phe His Arg Gln Ala Ser Lys
1               5                   10                  15

<210> SEQ ID NO 45
<211> LENGTH: 13
<212> TYPE: PRT
<213> ORGANISM: Artificial Sequence
<220> FEATURE:
<223> OTHER INFORMATION: Synthetic peptide PCSK9 fragment

<400> SEQUENCE: 45

Pro Glu Glu Asp Gly Thr Arg Phe His Arg Gln Ala Ser
1               5                   10
```

PCSK9 PEPTIDE COMBINATION VACCINE AND METHOD OF USE

CROSS-REFERENCE TO RELATED APPLICATIONS

This application is a division of U.S. application Ser. No. 14/344,879, filed Apr. 7, 2014 which is the U.S. national-stage of PCT filed PCT/EP2012/067950, filed Sep. 13, 2012.

STATEMENT REGARDING FEDERALLY SPONSORED RESEARCH OR DEVELOPMENT (Not Applicable)

REFERENCE TO MICROFICEH APPENDIX (Not Applicable)

BACKGROUND OF THE INVENTION

The present invention is associated with the development of a novel combined immunogenic peptide vaccine against PCSK9 derived from a combination of two different PCSK9 epitopes linked to an immunogenic carrier. The vaccine is established for the prevention and/or treatment of health disorders, caused by the hyperlipidemia, hypercholesterolemia and atherosclerosis.

Hyperlipidemia, hypercholesterolemia, hypertension and atherosclerosis are cardiovascular disorders considered as leading factors for the worldwide lethality. Together with factors such obesity, diabetes, smoking and lack of physical activity major factors for the development of cardiovascular alterations are genetic disorders such as autosomal dominant hypercholesterolemia (ADH). ADH is considered as an important factor for the development of cardiovascular disorders and is manifested by impaired cholesterol metabolism and increased of low density lipoprotein cholesterol, which subsequently leads to the formation of premature coronary artery disease (CAD).

It is known that three major genetic alterations could cause the development of ADH. The classical form of ADH is caused by mutations in the low density lipoprotein receptor (hereafter called LDLR). In addition, mutations in the apolipoprotein B-100 (apoB-100) and more specifically in its ligand-binding domain disrupt the binding of the ApoB-100 to LDLR, which subsequently leads to impaired cholesterol metabolism. Finally, the third and most recently discovered element which by genetic alterations could be involved in the development of the ADH is the proprotein convertase subtilisin/kexin type 9 (hereafter called PCSK9).

PCSK9, also known as neural apoptosis-regulated convertase 1 (NARC-1), is a proteinase K-like subtilase identified as the ninth member of the secretory subtilase family. The PCSK9 protein is synthesized as a ~72 kDa proprotein, which undergoes autocatalytically cleavage between the prodomain and catalytic domain leading consequently to the generation of the mature protein form. The prodomain (~14 kDa) remains bound to the mature protein 63 kDa and in this form the mature protein is proceeded towards the secretory pathway.

The role of PCSK9 in the lipid homeostasis is already well known. Not only that the expression of PCSK9 is regulated by the Sterol-Regulatory Element Binding Protein (hereafter called SREBP) in a similar manner to other SREBP-responsive genes involved in lipid homeostasis. But PCSK9 is also involved in the low density lipoprotein cholesterol (hereafter called LDLc) clearance by promoting LDLR internalization and degradation.

In vitro and in vivo studies highlighted the essential role of PCSK9 in the low density lipoprotein cholesterol uptake from the blood. On one side PCSK9 adenovirus overexpression significantly increased the levels of circulating LDLc, and on the other side PCSK9–/– mice showed a 2.8 fold increase in the levels of LDLR and reduction of LDLc compared to wild type animals.

The gene is localized at human chromosome 1p33-p34.3 and is expressed in tissues such as liver, kidney, cerebellum and small intestines. Many studies confirmed that "gain of function mutations" are causing decrease in the LDLR levels and a consequent hypercholesterolemia and predisposition to atherosclerosis. "Loss of function mutations" are increasing the levels of LDLR with a consequent decrease in low density lipoprotein cholesterol (LDLc).

Altogether, PCSK9 regulates LDLR levels posttranscriptionally and therefore is an attractive target for the treatment of atherosclerosis.

Meanwhile, numerous different strategies and approaches have been established to inhibit the function of PCSK9.

Application of siRNA against PCSK9 in monkeys (*Macaca fascicularis*) led to a significant reduction of total cholesterol. Other investigations with monoclonal and polyclonal antibodies against PCSK9 in mice and non-human primates succeeded to up-regulate LDLR with a concomitant decrease in the levels of total cholesterol and LDLc.

The reduction of PCSK9 levels by monoclonal or polyclonal antibody therapy or inactivation of PCSK9 upon small molecule inhibitors and knock out technology did not show any side effects in different animal models. Therefore, all in all PCSK9 is a very attractive target for the treatment of atherosclerosis.

WO 2011/027257 relates to immunogenic fragments derived from PCSK9 which can be used in a vaccine for the treatment, prevention and alleviation of PCSK9-mediated disorders.

In the WO 2009/100297 antagonists of human PCSK9 are disclosed.

WO 2010/057242 relates to vaccines which comprise peptides derived from a fragment of human PCSK9.

BRIEF SUMMARY OF THE INVENTION

An object of the present invention is to provide a peptide based vaccine against PCSK9 that is able to inhibit PCSK9 and abrogate/decrease the interaction of PCSK9 and LDLR. This leads to increased levels of LDLR in liver hepatocytes and subsequent reduction of total cholesterol and LDLc.

This object is achieved by a vaccine comprising a multiplicity (more than one, at least two) of fragments of Proprotein convertase subtilisin/kexin type 9 (PCSK9), wherein a first fragment of said at least two fragments comprises at least 8 consecutive amino acid residues of amino acid residues 150 to 170 and a second fragment of said at least two fragments comprises at least 8 consecutive amino acid residues of amino acid residues 205 to 225 of PCSK9 (SEQ ID NO:9.

BRIEF DESCRIPTION OF THE SEVERAL VIEWS OF THE DRAWING

The present invention is further illustrated in the following figures and examples without being restricted thereto.

DETAILED DESCRIPTION OF THE INVENTION

Figure 1:
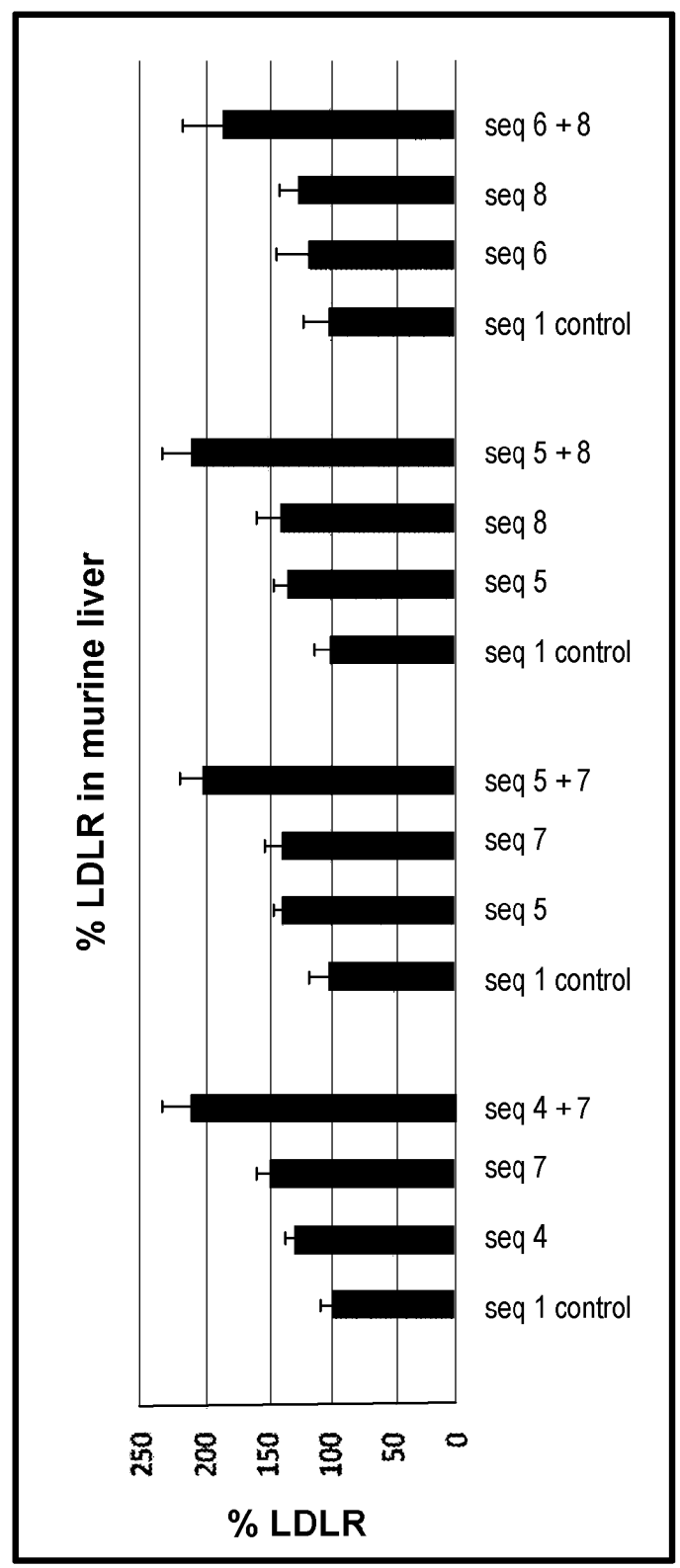
FIG. 1 shows the amount of low density lipoprotein receptor in liver lysates for peptides with Sequence ID No. 1 (irrelevant peptide control), 4, 5, 6, 7 and 8 and combination A (SEQ ID NO:4 and 7), B (SEQ ID NO:5 and 7), C (SEQ ID NO:5 and 8) and D (SEQ ID NO:6 and 8) compared to control animals.
Figure 2:
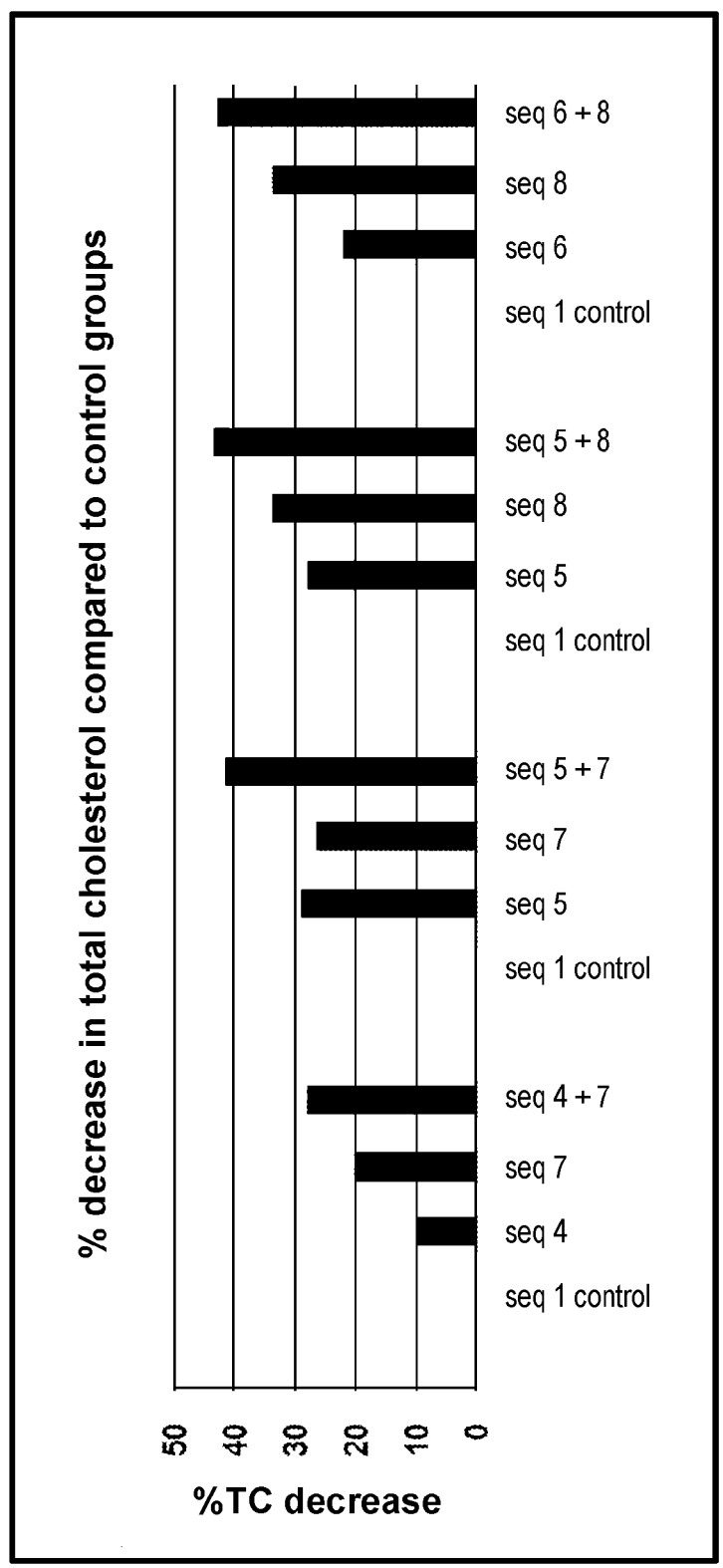
FIG. 2 shows the percent decrease of plasma levels of total cholesterol (n=5 mice per group) for peptides with Sequence ID No. 1 (irrelevant peptide control), 4, 5, 6, 7 and 8 and combination A (SEQ ID NO:4 and 7), B (SEQ ID NO:5 and 7), C (SEQ ID NO:5 and 8) and D (SEQ ID NO:6 and 8).

It turned surprisingly out that a vaccine comprising at least two different peptidic fragments of PCSK9 as defined above is able to increase the amount of LDL receptors much more efficiently compared to a vaccine comprising only one fragment of PCSK9. The administration of the vaccine of the present invention leads, for instance, to an increase in the levels of low density lipoprotein receptor in liver hepatocytes in vivo. As a consequence thereof, the mean values of LDLc and total cholesterol in blood plasma upon administration of vaccines decrease significantly. Therefore, the administration of a vaccine according to the present invention allows treating or preventing diseases caused by hyperlipidemia, hypercholesterolemia and/or atherosclerosis with a much higher efficiency and accuracy compared to the administration of the single peptides. In a preferred embodiment of the present invention all PCSK9 fragments of the vaccine of the present invention are derived from the PCSK9 fragments consisting of amino acid residues 150 to 170 and 205 to 225 of SEQ ID NO:9.

The peptidic fragments used in the vaccine of the present invention comprise at least 8, preferably at least 9, more preferably at least 10, consecutive amino acid residues of amino acid residues 150 to 170, preferably of amino acid residues 153 to 165, and 205 to 225, preferably of amino acid residues 209 to 222, of PCSK9 (SEQ ID NO:9).

```
                                         SEQ ID NO: 9
(PCSK9 amino acid sequence):
MGTVSSRRSW WPLPLLLLLL LLLGPAGARA QEDEDGDYEE

LVLALRSEED GLAEAPEHGT TATFHRCAKD PWRLPGTYVV

VLKEETHLSQ SERTARRLQA QAARRGYLTK ILHVFHGLLP

GFLVKMSGDL LELALKLPHV DYIEEDSSVF AQSIPWNLER

ITPPRYRADE YQPPDGGSLV EVYLLDTSIQ SDHREIEGRV

MVTDFENVPE EDGTRFHRQA SKCDSHGTHL AGVVSGRDAG

VAKGASMRSL RVLNCQGKGT VSGTLIGLEF IRKSQLVQPV

GPLVVLLPLA GGYSRVLNAA CQRLARAGVV LVTAAGNFRD

DACLYSPASA PEVITVGATN AQDQPVTLGT LGTNFGRCVD

LFAPGEDIIG ASSDCSTCFV SQSGTSQAAA HVAGIAAMML

SAEPELTLAE LRQRLIHFSA KDVINEAWFP EDQRVLTPNL

VAALPPSTHG AGWQLFCRTV WSAHSGPTRM ATAVARCAPD

EELLSCSSFS RSGKRRGERM EAQGGKLVCR AHNAFGGEGV

YAIARCCLLP QANCSVHTAP PAEASMGTRV HCHQQGHVLT

GCSSHWEVED LGTHKPPVLR PRGQPNQCVG HREASIHASC

CHAPGLECKV KEHGIPAPQE QVTVACEEGW TLTGCSALPG

TSHVLGAYAV DNTCVVRSRD VSTTGSTSEG AVTAVAICCR

SRHLAQASQE LQ
```

The fragments derived from PCSK9 comprise or consist of preferably 8 to 20, more preferably 10 to 15, amino acid residues. According to a particularly preferred embodiment of the present invention the peptides derived from amino acid residues 150 to 170 of PCSK9 comprise 8 to 15, preferably 10 to 13, amino acid residues. The peptides derived from amino acid residues 205 to 225 of PCSK9 comprise 8 to 16, preferably 10 to 14, amino acid residues.

The vaccine of the present invention is a combination of at least 2, preferably at least 3, more preferably at least 4, even more preferably at least 5, peptides derived from amino acid residues 150 to 170 and 205 to 225 of PCSK9 (SEQ ID NO:9). This combination comprises at least two sequences with different epitope origin.

The peptides of the present invention can be chemically synthesized by methods which are well known in the art. Of course it is also possible to produce the peptides of the present invention using recombinant methods. The peptides can be produced in microorganisms such as bacteria, yeast or fungi, in eukaryotic cells such as mammalian or insect cells, or in a recombinant virus vector such as adenovirus, poxvirus, herpes virus, Simliki forest virus, baculovirus, bacteriophage, sindbis virus or Sendai virus. Suitable bacteria for producing the peptides include *E. coli*, *B. subtilis* or any other bacterium that is capable of expressing such peptides. Suitable yeast cells for expressing the peptides of the present invention include *Saccharomyces cerevisiae*, *Schizosaccharomyces pombe*, *Candida*, *Pichia pastoris* or any other yeast capable of expressing peptides. Corresponding means and methods are well known in the art. Also methods for isolating and purifying recombinantly produced peptides are well known in the art and include e.g. gel filtration, affinity chromatography, ion exchange chromatography etc.

To facilitate isolation of the peptides of the present invention, fusion polypeptides may be made wherein the peptides are translationally fused (covalently linked) to a heterologous polypeptide which enables isolation by affinity chromatography. Typical heterologous polypeptides are His-Tag (e.g. His$_6$; 6 histidine residues), GST-Tag (Glutathione-S-transferase) etc. The fusion polypeptide facilitates not only the purification of the peptides but can also prevent the degradation of the peptides during the purification steps. If it is desired to remove the heterologous polypeptide after purification the fusion polypeptide may comprise a cleavage site at the junction between the peptide and the heterologous polypeptide. The cleavage site may consist of an amino acid sequence that is cleaved with an enzyme specific for the amino acid sequence at the site (e.g. proteases).

According to the present invention at least one fragment is derived from amino acid residues 150 to 170 and at least one fragment is derived from amino acid residues 205 to 225 of PCSK9 (SEQ ID NO:9).

The vaccine of the present invention comprises PCSK9 fragments of different parts of the PCSK9 protein. Therefore, it is particularly preferred that at least one fragment is derived from one specific PCSK9 fragment, whereas at least one fragment is derived from another specific PCSK9 fragment.

According to another preferred embodiment of the present invention the at least two fragments of PCSK9 are selected from the group consisting of peptides having amino acid sequence SIPWNLERITPPR (SEQ ID NO:2), PEEDGTRFHRQASK (SEQ ID NO:3), PEEDGTRFHRQA (SEQ ID NO:4), EEDGTRFHRQASK (SEQ ID NO:5), EEDGTRFHRQAS (SEQ ID NO:6), SIPWNLERITP (SEQ ID NO:7) and SIPWNLERIT (SEQ ID NO:8).

The at least two fragments of PCSK9 may also consist of or comprise an amino acid sequence selected from the group consisting of FAQSIPWNLERITPPRYRAD (SEQ ID NO:10), FAQSIPWNLERITPPRYRA (SEQ ID NO:11), FAQSIPWNLERITPPRYR (SEQ ID NO:12), FAQSIPWNLERITPPRY (SEQ ID NO:13), FAQSIPWNLERITPPR (SEQ ID NO:14), FAQSIPWNLERITPP (SEQ ID NO:15), AQSIPWNLERITPPRYRAD (SEQ ID NO:16), QSIPWNLERITPPRYRAD (SEQ ID NO:17), SIPWNLERITPPRYRAD (SEQ ID NO:18), AQSIPWNLERITPPRYRA (SEQ ID NO:19), QSIPWNLERITPPRYRA (SEQ ID NO:20), SIPWNLERITPPRYRA (SEQ ID NO:21), AQSIPWNLERITPPRYR (SEQ ID NO:22), QSIPWNLERITPPRYR (SEQ ID NO:23), SIPWNLERITPPRYR (SEQ ID NO:24), QSIPWNLERITPPRY (SEQ ID NO:25), SIPWNLERITPPRY (SEQ ID NO:26), AQSIPWNLERITPPR (SEQ ID NO:27), QSIPWNLERITPPR (SEQ ID NO:28), SIPWNLERITPP (SEQ ID NO:29), ENVPEEDGTRFHRQASKCDS (SEQ ID NO:30), ENVPEEDGTRFHRQASKCD (SEQ ID NO:31), ENVPEEDGTRFHRQASKC (SEQ ID NO:32), ENVPEEDGTRFHRQASK (SEQ ID NO:33), NVPEEDGTRFHRQASKCDS (SEQ ID NO:34), VPEEDGTRFHRQASKCDS (SEQ ID NO:35), PEEDGTRFHRQASKCDS (SEQ ID NO:36), NVPEEDGTRFHRQASKCD (SEQ ID NO:37), VPEEDGTRFHRQASKCD (SEQ ID NO:38), PEEDGTRFHRQASKCD (SEQ ID NO:39), NVPEEDGTRFHRQASKC (SEQ ID NO:40), VPEEDGTRFHRQASKC (SEQ ID NO:41), PEEDGTRFHRQASKC (SEQ ID NO:42), NVPEEDGTRFHRQASK (SEQ ID NO:43), VPEEDGTRFHRQASK (SEQ ID NO:44), PEEDGTRFHRQAS (SEQ ID NO:45).

The at least one fragment of PCSK9 has preferably an amino acid sequence selected from the group consisting of SIPWNLERITPPR (SEQ ID NO:2), SIPWNLERITP (SEQ ID NO:7) and SIPWNLERIT (SEQ ID NO:8) and at least one fragment of PCSK9 has an amino acid sequence selected from the group consisting of PEEDGTRFHRQASK (SEQ ID NO:3), PEEDGTRFHRQA (SEQ ID NO:4), EEDGTRFHRQASK (SEQ ID NO:5) and EEDGTRFHRQAS (SEQ ID NO:6).

According to a preferred embodiment of the present invention the vaccine of the present invention comprises SIPWNLERITPPR (SEQ ID NO: 2)
and

PEEDGTRFHRQASK, (SEQ ID NO: 3)

SIPWNLERITPPR (SEQ ID NO: 2)
and

PEEDGTRFHRQA, (SEQ ID NO: 4)

SIPWNLERITPPR (SEQ ID NO: 2)
and

EEDGTRFHRQASK, (SEQ ID NO: 5)

SIPWNLERITPPR (SEQ ID NO: 2)
and

EEDGTRFHRQAS, (SEQ ID NO: 6)

PEEDGTRFHRQASK (SEQ ID NO: 3)
and

SIPWNLERITP, (SEQ ID NO: 7)

PEEDGTRFHRQASK (SEQ ID NO: 3)
and

SIPWNLERIT, (SEQ ID NO: 8)

PEEDGTRFHRQA (SEQ ID NO: 4)
and

SIPWNLERITP, (SEQ ID NO: 7)

PEEDGTRFHRQA (SEQ ID NO: 4)
and

SIPWNLERIT, (SEQ ID NO: 8)

EEDGTRFHRQASK (SEQ ID NO: 5)
and

SIPWNLERITP, (SEQ ID NO: 7)

EEDGTRFHRQASK (SEQ ID NO: 5)
and

SIPWNLERIT, (SEQ ID NO: 8)

EEDGTRFHRQAS (SEQ ID NO: 6)
and

SIPWNLERITP (SEQ ID NO: 7)
or

EEDGTRFHRQAS (SEQ ID NO: 6)
and

SIPWNLERIT, (SEQ ID NO: 8)

whereby a vaccine comprising

PEEDGTRFHRQA (SEQ ID NO: 4)
and

SIPWNLERITP, (SEQ ID NO: 7)

-continued

EEDGTRFHRQASK (SEQ ID NO: 5)
and

SIPWNLERITP, (SEQ ID NO: 7)

EEDGTRFHRQASK (SEQ ID NO: 5)
and

SIPWNLERIT (SEQ ID NO: 8)
or

EEDGTRFHRQAS (SEQ ID NO: 6)
and

SIPWNLERIT is particularly preferred. (SEQ ID NO: 8)

The at least two fragments of PCSK9 preferably comprise a cysteine residue at (bound to) the C- and/or N-terminal end.

The provision of a cysteine residue at the N- and/or C-terminus of a peptide may facilitate its conjugation to a carrier, for instance, and/or may enhance the immunogenicity of the peptide.

According to a preferred embodiment of the present invention the at least two fragments of PCSK9 (i.e. the at least two peptides derived from PCSK9) are coupled, individually or in combination, to a pharmaceutically acceptable carrier, preferably KLH (Keyhole Limpet Hemocyanin).

According to a preferred embodiment of the present invention the at least two fragments of PCSK9 are coupled to a pharmaceutically acceptable carrier, preferably KLH (Keyhole Limpet Hemocyanin), tetanus toxoid, albumin-binding protein, hepatitis B core antigen, bovine serum albumin, a dendrimer (MAP), peptide linkers (or flanking regions) as well as the adjuvant substances described in Singh et al., Nat. Biotech. (1999), 1075-1081 (in particular those in Table 1 of that document), and O'Hagan et al., Nature Reviews, Drug Discovery (9) (2003), 727-735 (in particular the endogenous immuno-potentiating compounds and delivery systems described therein), or mixtures thereof. The conjugation chemistry (e.g. via heterobifunctional compounds such as GMBS and of course also others as described in "Bioconjugate Techniques", Greg T. Hermanson) in this context can be selected from reactions known to the skilled man in the art. Moreover, the vaccine composition may be formulated with an adjuvant, preferably a low soluble aluminum composition, in particular aluminum hydroxide. Of course, also adjuvants like MF59 aluminum phosphate, calcium phosphate, cytokines (e.g., IL-2, IL-12, GM-CSF), saponins (e.g., QS21), MDP derivatives, CpG oligonucleotides, LPS, MPL, polyphosphazenes, emulsions (e.g., Freund's, SAF), liposomes, lipopeptides, virosomes, iscoms, cochleates, PLG microparticles, poloxamer particles, virus-like particles, heat-labile enterotoxin (LT), cholera toxin (CT), mutant toxins (e.g., LTK63 and LTR72), microparticles and/or polymerized liposomes may be used.

The peptides of the present invention are preferably bound to the carrier or adjuvant via a linker, which is selected from the group consisting of NHS-poly (ethylene oxide) (PEO) (e.g. NHS-PEO$_4$-maleimide).

A vaccine which comprises a peptide of the present invention and the pharmaceutically acceptable carrier may be administered by any suitable mode of application, e.g. intradermally (i.d.), intraperitoneally (i.p.), intramuscularly (i.m.), intranasally, orally, subcutaneously (s.c.), etc. and in any suitable delivery device (O'Hagan et al., Nature Reviews, Drug Discovery 2 (9), (2003), 727-735). The compound of the present invention is preferably formulated for intradermal, subcutaneous or intramuscular administration. Means and methods for obtaining respective formulations are known to the person skilled in the art (see e.g. "Handbook of Pharmaceutical Manufacturing Formulations", Sarfaraz Niazi, CRC Press Inc, 2004).

Thus, the vaccine according to the present invention comprises at least two peptides which are preferably formulated for intradermal, subcutaneous or intramuscular administration.

The at least two peptides/fragments in the vaccine of the present invention are preferably formulated with an adjuvant, preferably aluminum hydroxide.

According to a preferred embodiment of the present invention the vaccine is used in the treatment and/or prevention of disorders caused by hyperlipidemia, hypercholesterolemia and/or atherosclerosis, preferably cardiovascular diseases, stroke or peripheral vascular diseases.

As outlined, the above mentioned peptides and the combinations thereof are able to induce the formation of antibodies which are able to bind specifically PCSK9. The interaction of the antibodies with PCSK9 leads to the increase of low density lipoprotein receptor in liver hepatocytes in vivo and subsequent reduction of the plasma total cholesterol levels.

The disease associated with atherosclerosis is preferably selected from the group consisting of peripheral arterial occlusive disease, coronary heart disease, apoplectic cerebral insultus and stroke.

The terms "diseases associated with hyperlipidemia, hypercholesterolemia and/or atherosclerosis" and "disorders caused by hyperlipidemia, hypercholesterolemia and/or atherosclerosis" refer to diseases which are a consequence of hyperlipidemia, hypercholesterolemia and atherosclerosis. These diseases include among others peripheral arterial occlusive disease, coronary heart disease and apoplectic cerebral insultus (see e.g. Steinberg, D. J Lipid Res 46(2005):179-190 and Steinberg, D. J Lipid Res 47(2006): 1339-1351).

According to a preferred embodiment of the present invention the at least two fragments of PCSK9 are administered to an individual in an amount of 0.1 ng to 10 mg, preferably of 0.5 to 500 µg, more preferably 1 to 100 µg, per immunization. In a preferred embodiment these amounts refer to all fragments of PCSK9 present in the vaccine. In another preferred embodiment these amounts refer to each single fragment present in the vaccine. It is of course possible to provide a vaccine in which the specific fragments of PCSK9 are present in different or equal amounts. However, the peptide of the present invention may alternatively be administered to an individual in an amount of 0.1 ng to 10 mg, preferably 10 ng to 1 mg, in particular 100 ng to 300 µg/kg body weight.

The amount of peptides that may be combined with the carrier materials to produce a single dosage form will vary depending upon the host treated and the particular mode of administration. The dose of the vaccine may vary according to factors such as the disease state, age, sex and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances. For instance, the peptides and vaccine of the present invention may be administered to an individual at intervals of several days, one or two weeks or even months or years depending always on the level of antibodies directed to PCSK9.

In a preferred embodiment of the present invention the peptide/vaccine is applied between 2 and 10, preferably between 2 and 7, even more preferably up to 5 and most preferably up to 4 times. This number of immunizations may lead to a basic immunisation. In a particularly preferred embodiment the time interval between the subsequent vaccinations is chosen to be between 2 weeks and 5 years, preferably between 1 month and up to 3 years, more preferably between 2 months and 1.5 years. An exemplified vaccination schedule may comprise 3 to 4 initial vaccinations over a period of 6 to 8 weeks and up to 6 months. Thereafter the vaccination may be repeated every two to ten years. The repeated administration of the peptide/vaccine of the present invention may maximize the final effect of a therapeutic vaccination.

The vaccine of the present invention may also comprise antigens derived from other proteins which are also involved in the regulation of the LDL and/or HDL levels within a human body. For instance, the PCSK9 fragments of the present invention may be combined with epitopes derived from human CETP protein.

Typically, the vaccine contains the peptides of the present invention in an amount of 0.5 to 500 µg, preferably 1 to 100 µg and alternatively from 0.1 ng to 10 mg, preferably 10 ng to 1 mg, in particular 100 ng to 100 µg, or, alternatively, e.g. 100 fmol to 10 µmol, preferably 10 µmol to 1 µmol, in particular 100 µmol to 100 nmol. Typically, the vaccine may also contain auxiliary substances, e.g. buffers, stabilizers etc.

According to a preferred embodiment of the present invention relates to the use of two or more peptides. According to the present invention for the manufacture of a vaccine for preventing and/or treating of atherosclerosis and diseases associated with atherosclerosis, wherein the disease associated with atherosclerosis is preferably selected from the group consisting of peripheral arterial occlusive disease, coronary heart disease, apoplectic cerebral insultus and stroke.

Yet another aspect of the present invention relates to a method for treating an individual suffering or at risk to suffer from atherosclerosis or a disease associated with atherosclerosis in the course of which a peptide or vaccine according to the present invention is administered to said individual.

Next to the vaccine of the present invention, the individual to be treated may receive also other active ingredients known to influence the LDL and/or HDL levels in humans and mammals such as statins, fibrates, nicotinic acid, cholesterol uptake inhibitor (e.g. ezetimibe), ApoA1 Milano, delipidated HDL, plant sterols. It is particularly preferred to administers to an individual the vaccine of the present invention together (i.e. at the same time, consecutively etc.) with statins.

Examples

Materials and Methods

Vaccine:

The peptides were conjugated via the heterobifunctional linker GMBS (4-Maleimidobutyric acid N-hydroxysuccinimide ester) to KLH (Keyhole Limpet Hemocyanin).

15 µg of the peptides were suspended with aluminum hydroxide (end concentration of aluminum hydroxide was 0.2%). As buffer phosphate was used.

TABLE 1

Sequences used for the vaccine production

| | Amino acid sequence | Sequence Information |
|---|---|---|
| SEQ ID NO: 1 | RPETWIPNRSPIL | irrelevant (control group) |
| SEQ ID NO: 2 | SIPWNLERITPPR | aa 153-165 of SEQ ID NO: 9 |
| SEQ ID NO: 3 | PEEDGTRFHRQASK | aa 209-222 of SEQ ID NO: 9 |
| SEQ ID NO: 4 | PEEDGTRFHRQA | aa 209-220 of SEQ ID NO: 9 |
| SEQ ID NO: 5 | EEDGTRFHRQASK | aa 210-222 of SEQ ID NO: 9 |
| SEQ ID NO: 6 | EEDGTRFHRQAS | aa 210-221 of SEQ ID NO: 9 |
| SEQ ID NO: 7 | SIPWNLERITP | aa 153-163 of SEQ ID NO: 9 |
| SEQ ID NO: 8 | SIPWNLERIT | aa 153-162 of SEQ ID NO: 9 |
| Combination A (SEQ ID NO: 4 and 7) | PEEDGTRFHRQA + SIPWNLERITP | aa 209-220 + aa 153-163 of SEQ ID NO: 9 |
| Combination B (SEQ ID NO: 5 and 7) | EEDGTRFHRQASK + SIPWNLERITP | aa 210-222 + aa 153-163 of SEQ ID NO: 9 |
| Combination C (SEQ ID NO: 5 and 8) | EEDGTRFHRQASK + SIPWNLERIT | aa 210-222 + aa 153-162 of SEQ ID NO: 9 |
| Combination D (SEQ ID NO: 6 and 8) | EEDGTRFHRQAS + SIPWNLERIT | aa 210-221 + aa 153-162 of SEQ ID NO: 9 |

Animal Experiments:

5 Balb/c mice were subcutaneously immunized. Mice had access to food and water ad libitum and were kept under a 12 h light/dark cycle. Age of mice at the beginning of experiments was usually 8 to 10 weeks.

Mice were injected four times in 2 week intervals with 15 µg of net peptide coupled to KLH and adsorbed to Alum as adjuvant in a volume of 1 ml in total via the s.c. route.

Blood was taken approximately 2 weeks after the final injection.

Protein ELISA:

To determine the immunogenicity of the vaccines, 96-well Nunc-Maxisorb plates were coated with recombinant human PCSK9 protein. Unspecific binding was blocked by incubation with blocking buffer (1% BSA in PBS). Appropriate serum dilutions were added to the wells serially diluted 1:2 fold and incubated for approximately 1 hour at 37° C. On every ELISA plate a standard serum was included as internal control. Bound antibodies were detected by incubation with biotinylated goat anti-mouse IgG, followed by horseradish peroxidase coupled to Streptavidin. As substrate ABTS was added and the optical density (OD) at 405 nm was measured in a Microwell plate-reader. As negative control sera from the control group injected with an irrelevant peptide were analyzed. The titers were defined as the dilution of the serum where 50% of the ODmax in the assay are reached.

Total Cholesterol Assay

Total cholesterol was measured with the WAKO LabAssay™ Cholesterol Kit (Wako).

LDLR Sandwich ELISA

To determine the levels of low density lipoprotein receptor (LDLR) in murine liver, mice were sacrificed 2 weeks after the last vaccination. Liver tissue was isolated and protein extraction was done according to standard protocols.

96 well Nunc-Maxisorb plates were coated with mouse LDLR affinity purified goat polyclonal anti-LDLR antibody (R&D Systems). Unspecific binding was blocked by incubation with 1% BSA/PBS. Subsequently, the liver lysates were incubated for 3 h at room temperature to capture the murine LDLR. The detection of captured LDLR was done by chicken polyclonal anti-LDLR antibody (Abcam) followed by incubation with a secondary biotinylated goat anti-chicken IgG (Southern Biotech) and by streptavidin-HRP conjugate. Finally, TMB was used as a peroxidase chromogen substrate.

The quantification of low density lipoprotein receptor was done by comparison to a standard calibration curve and was normalized to the total protein concentration of the lysates.

The control group (irrelevant peptide control vaccination) has been set to 100%, and the levels of groups treated with anti-PCSK9 vaccines were compared to this control group.

Example 1

Median protein titers against human PCSK9. (n=5 mice per group).

| Sequence ID | Median Protein Titer OD max/2 |
|---|---|
| seq 1 control | 0 |
| seq 4 | 45.000 |
| seq 7 | 47.000 |
| seq 5 | 14.000 |
| seq 7 | 47.000 |
| seq 5 | 14.000 |
| seq 8 | 31.000 |
| seq 6 | 13.000 |
| seq 8 | 31.000 |

Example 2

Mean values in mg/dL and percentage of decrease of total cholesterol. (n=5 mice per group).

| | Sequence ID | Mean Values (mg/dl) | Stdv | % TC decrease compared to control group |
|---|---|---|---|---|
| Combination A | 1 (control) | 98 | 9 | |
| | 4 | 88 | 12 | 10 |
| | 7 | 78 | 4 | 20 |
| | 4 + 7 | 71 | 5 | 28 |
| Combination B | 1 (control) | 86 | 9 | |
| | 5 | 61 | 7 | 29 |
| | 7 | 64 | 5 | 26 |
| | 5 + 7 | 51 | 1 | 41 |
| Combination C | 1 (control) | 83 | 7 | |
| | 5 | 60 | 8 | 28 |
| | 8 | 55 | 3 | 34 |
| | 5 + 8 | 47 | 7 | 43 |
| Combination D | 1 (control) | 83 | 7 | |
| | 6 | 65 | 4 | 22 |
| | 8 | 55 | 3 | 34 |
| | 6 + 8 | 48 | 4 | 42 |

Example 3

Amount of low density lipoprotein receptor in mouse liver in vivo (n=5 mice per group), compared to the control group.

| | Sequence ID | % LDLR | Stdv |
|---|---|---|---|
| Combination A | 1 (control) | 100 | 8 |
| | 4 | 130 | 8 |
| | 7 | 148 | 12 |
| | 4 + 7 | 212 | 24 |
| Combination B | 1 (control) | 100 | 19 |
| | 5 | 140 | 6 |
| | 7 | 140 | 14 |
| | 5 + 7 | 202 | 18 |
| Combination C | 1 (control) | 100 | 13 |
| | 5 | 135 | 12 |
| | 8 | 143 | 17 |
| | 5 + 8 | 212 | 21 |
| Combination D | 1 (control) | 100 | 22 |
| | 6 | 116 | 27 |
| | 8 | 125 | 14 |
| | 6 + 8 | 187 | 30 |

The invention claimed is:

1. An immunogen comprising at least two separate fragments of Proprotein convertase subtilisin/kexin type 9 (PCSK9),
    wherein a first fragment of said at least two fragments comprises at least 8 consecutive amino acid residues of amino acid residues 150 to 170, and
    wherein a second fragment of said at least two fragments comprises at least 8 consecutive amino acid residues of amino acid residues 205 to 225 of PCSK9 (SEQ ID NO: 9).

2. The immunogen of claim 1,
    wherein the first fragment of said at least two fragments comprises at least 9 consecutive amino acid residues of amino acid residues 150 to 170, and
    wherein the second fragment of said at least two fragments comprises at least 9 consecutive amino acid residues of amino acid residues 205 to 225 of PCSK9 (SEQ ID NO: 9).

3. The immunogen of claim 1,
    wherein the first fragment of said at least two fragments comprises at least 10 consecutive amino acid residues of amino acid residues 150 to 170, and
    wherein a second fragment of said at least two fragments comprises at least 10 consecutive amino acid residues of amino acid residues 205 to 225 of PCSK9 (SEQ ID NO: 9).

4. The immunogen of claim 1,
    wherein the first fragment of said at least two fragments comprises at least 15 consecutive amino acid residues of amino acid residues 150 to 170, and
    wherein the second fragment of said at least two fragments comprises at least 15 consecutive amino acid residues of amino acid residues 205 to 225 of PCSK9 (SEQ ID NO: 9).

5. The immunogen according to claim 1, wherein at least one fragment comprises at least 8 continuous residues of SIPWNLERITPPR (SEQ ID NO: 2), SIPWNLERITP (SEQ ID NO: 7) or SIPWNLERIT (SEQ ID NO: 8); and at least one other fragment consists of at least 8 contiguous residues of PEEDGTRFHRQASK (SEQ ID NO: 3), PEEDGTRFHRQA (SEQ ID NO: 4), EEDGTRFHRQASK (SEQ ID NO: 5), or EEDGTRFHRQAS (SEQ ID NO: 6).

6. The immunogen according to claim 1, wherein at least one fragment consists of at least 8 continuous residues of SIPWNLERITPPR (SEQ ID NO: 2), SIPWNLERITP (SEQ ID NO: 7) or SIPWNLERIT (SEQ ID NO: 8); and at least one other fragment consists of at least 8 contiguous residues of PEEDGTRFHRQASK (SEQ ID NO: 3), PEEDGTRFHRQA (SEQ ID NO: 4), EEDGTRFHRQASK (SEQ ID NO: 5), or EEDGTRFHRQAS (SEQ ID NO: 6).

7. The immunogen according to claim 1, wherein the immunogen comprises the following pairs of separate fragments:

```
                                          (SEQ ID NO: 2)
            SIPWNLERITPPR
            and
                                          (SEQ ID NO: 3)
            PEEDGTRFHRQASK, (SEQ ID NO: 2)
            SIPWNLERITPPR
            and
                                          (SEQ ID NO: 4)
            PEEDGTRFHRQA, (SEQ ID NO: 2)
            SIPWNLERITPPR
            and
                                          (SEQ ID NO: 5)
            EEDGTRFHRQASK, (SEQ ID NO: 2)
            SIPWNLERITPPR
            and
```

-continued

EEDGTRFHRQAS, (SEQ ID NO: 6)

PEEDGTRFHRQASK (SEQ ID NO: 3)
and

SIPWNLERITP, (SEQ ID NO: 7)

PEEDGTRFHRQASK (SEQ ID NO: 3)
and

SIPWNLERIT, (SEQ ID NO: 8)

PEEDGTRFHRQA (SEQ ID NO: 4)
and

SIPWNLERITP, (SEQ ID NO: 7)

PEEDGTRFHRQA (SEQ ID NO: 4)
and

SIPWNLERIT, (SEQ ID NO: 8)

EEDGTRFHRQASK (SEQ ID NO: 5)
and

SIPWNLERITP, (SEQ ID NO: 7)

EEDGTRFHRQASK (SEQ ID NO: 5)
and

SIPWNLERIT, (SEQ ID NO: 8)

EEDGTRFHRQAS (SEQ ID NO: 6)
and

SIPWNLERITP (SEQ ID NO: 7)
or

EEDGTRFHRQAS (SEQ ID NO: 6)
and

SIPWNLERIT. (SEQ ID NO: 8)

8. The immunogen according to claim 1, wherein the at least two fragments of PCSK9 comprise a cysteine residue at the C- and/or N-terminal end.

9. The immunogen according to claim 1, wherein the at least two fragments of PCSK9 are coupled to Keyhole limpet hemocyanin ("KLH") or another pharmaceutically acceptable carrier.

10. The immunogen according to claim 1, wherein the at least two fragments of PCSK9 are formulated for intradermal, subcutaneous or intramuscular administration.

11. The immunogen according to claim 1, further comprising at least aluminum hydroxide or another adjuvant.

12. The immunogen according to claim 1, wherein said first fragment consists of the amino acid residues 150-170 of PCSK9 (SEQ ID NO: 9) and the second fragment consists of the amino acid residues 205-225 of PCSK9 (SEQ ID NO: 9).

13. The immunogen according to claim 1, wherein said first fragment consists of 8 to 20 amino acid residues of residues 150-170 of PCSK9 (SEQ ID NO: 9) and the second fragment consists of 8 to 20 amino acid residues of residues 205-225 of PCSK9 (SEQ ID NO: 9); wherein the first and/or second fragments optionally have a cysteine residue bound to their N and/or C-terminal(s).

14. The immunogen according to claim 1, wherein said first fragment consists of 8 to 20 amino acid residues of residues 150-170 of PCSK9 (SEQ ID NO: 9) and the second fragment consists of 8 to 20 amino acid residues of residues 205-225 of PCSK9 (SEQ ID NO: 9); wherein at least one of the first and/or second fragments has a cysteine residue bound to its N and/or C-terminal(s).

15. The immunogen according to claim 1, wherein said first fragment consists of 8 to 20 amino acid residues of residues 150-170 of PCSK9 (SEQ ID NO: 9) and the second fragment consists of 8 to 20 amino acid residues of residues 205-225 of PCSK9 (SEQ ID NO: 9); wherein at least one of the first and/or second fragments further comprises amino acid residues heterologous to PCSK9 (SEQ ID NO: 9).

16. The immunogen according to claim 1, wherein said first fragment consists of 8 to 20 amino acid residues of residues 153-165 of PCSK9 (SEQ ID NO: 9) and the second fragment consists of 8 to 20 amino acid residues of residues 209-222 of PCSK9 (SEQ ID NO: 9); wherein at least one of the first and/or second fragments have a cysteine residue bound to their N and/or C-terminal(s).

17. A process for treating and/or preventing at least one disorder caused by hyperlipidemia, hypercholesterolemia and/or atherosclerosis, comprising administering the immunogen of claim 1 to a subject in need thereof.

18. The process of claim 17, wherein the at least two peptide fragments of PCSK9 are administered in an amount of 0.1 ng to 10 mg per dose to the subject.

19. The process of claim 17 comprising administering said immunogen intradermally, subcutaneously, or intramuscularly.

20. A process for increasing an amount of LDL receptors or for reducing a mean value of LDLc and total cholesterol in a subject in need thereof comprising administering the immunogen of claim 1 to a subject in need thereof.

* * * * *